United States Patent
Benavides et al.

(10) Patent No.: US 7,105,504 B2
(45) Date of Patent: *Sep. 12, 2006

(54) COMBINATION OF A CB1 RECEPTOR ANTAGONIST AND OF A PRODUCT WHICH ACTIVATES DOPAMINERGIC NEUROTRANSMISSION IN THE BRAIN, THE PHARMACEUTICAL COMPOSITIONS COMPRISING THEM AND THEIR USE IN THE TREATMENT OF PARKINSON'S DISEASE

(75) Inventors: Jésus Benavides, Chatenay Malabry (FR); Daniel Boccio, Pringy (FR); Yvette Henin, Paris (FR); Odile Piot-Grosjean, Choisy le Roi (FR)

(73) Assignee: Aventis Pharma S.A., Cedex (FR)

( * ) Notice: Subject to any disclaimer, the term of this patent is extended or adjusted under 35 U.S.C. 154(b) by 79 days.

This patent is subject to a terminal disclaimer.

(21) Appl. No.: 10/786,483

(22) Filed: Feb. 25, 2004

(65) Prior Publication Data

US 2005/0107356 A1    May 19, 2005

Related U.S. Application Data

(63) Continuation of application No. PCT/FR02/02945, filed on Aug. 28, 2002.

(30) Foreign Application Priority Data

Aug. 29, 2001  (FR) .................................. 01 11201

(51) Int. Cl.
| | |
|---|---|
| *A01N 43/00* | (2006.01) |
| *A01N 37/10* | (2006.01) |
| *A01N 43/40* | (2006.01) |
| *A01N 43/78* | (2006.01) |
| *A61K 31/397* | (2006.01) |

(52) U.S. Cl. ........................ 514/210.01; 514/210.16; 514/252.12; 514/570; 514/323; 514/367

(58) Field of Classification Search ........... 514/210.01, 514/210.16
See application file for complete search history.

(56) References Cited

U.S. PATENT DOCUMENTS

2001/0027193 A1 * 10/2001 Achard et al. ......... 514/210.01
2002/0177593 A1 * 11/2002 Ishihara et al. .......... 514/227.5

OTHER PUBLICATIONS

Brotchie, J.M., The Cannabinoid Receptor Antagonist SR141716A Reduces L-DOPA-Induced Dyskinesia in the MPTP-Treated Primate Model of Parkinson's Disease, British Journal of Pharmacology (1998, vol. 123, pp. 66P).
Clara Sanudo-Pena et al., A Novel Neurotransmitter System Involved in the Control of Motor Behavior by the Basal Ganglia, Ann. New York Academy of Sciences, (1998, vol. 860, pp. 475-479).
Justin P. Meschler et al., D2, but not D1 Dopamine Receptor Agonists Potentiate Cannabinoid-Induced Sedation In Nonhuman Primates 1,2 Journal of Pharmaclology And Experimental Therapeutics, (2000, vol. 292, Issue 3, pp. 952-959).
Vincenzo Di Marzo et al., Enhanced Levels of Endogenous Cannabinoids in the Globus Pallidus are Associated with a Reduction in Movement in an animal model of Parkinson's Disease, FASEB Journal (2000, vol. 14, Issue 10, pp. 1432-1438).

* cited by examiner

*Primary Examiner*—Shengjun Wang
*Assistant Examiner*—Yong S. Chong
(74) *Attorney, Agent, or Firm*—Balaram Gupta

(57) ABSTRACT

The present invention relates to the combination of one or more CB1 antagonist azetidine derivatives and of one or more products which activate dopaminergic neurotransmission in the brain, to the pharmaceutical compositions comprising them and to their use in the treatment of Parkinson's disease.

22 Claims, No Drawings

COMBINATION OF A CB1 RECEPTOR ANTAGONIST AND OF A PRODUCT WHICH ACTIVATES DOPAMINERGIC NEUROTRANSMISSION IN THE BRAIN, THE PHARMACEUTICAL COMPOSITIONS COMPRISING THEM AND THEIR USE IN THE TREATMENT OF PARKINSON'S DISEASE

This application is a continuation of International application No. PCT/FR02/02,945, filed Aug. 28, 2002; which claims the benefit of priority of French Patent Application No. 01/11,201, filed Aug. 29, 2001.

BACKGROUND OF THE INVENTION

1. Field of the Invention

The present invention relates to the combination of one or more CB1 receptor antagonists and of one or more products which activate dopaminergic neurotransmission in the brain, to the pharmaceutical compositions comprising them and to their use in the treatment of Parkinson's disease.

2. Description of the Art

CB1 receptor antagonists have been developed for the treatment of schizophrenia (D. Kendall, Curr. Opin. Cent. Peripher. Nerv. Syst. Invest. Drugs, 2(1), 112–122, 2000), for their effect on food intake (G. Colombo et al., Life Sciences, 63 (8), 113–117 (1998); J. Siamand et al., Behavioral Pharmacol., 9, 179–181 (1998)) and for the treatment of Parkinson's disease, epilepsy, migraine and stress (G. Gerdeman, D M. Lovinger, J. Neurophysiol., 85(1), 468–471, 2001; WO 0046209).

Parkinson's disease results from a chronic and progressive neurological disorder. It is due to a deficiency of dopamine and a relative excess of acetylcholine and is associated with destruction of the dopaminergic neurons which participate in the control of the motor activities (H. Lullmann et al., Atlas de poche de pharmacologie [Pocket atlas of pharmacology], 2nd Ed., Médecine-Sciences, Flammarion, ISBN2-257-12119-8). The treatment of Parkinson's disease is mainly pharmacological and involves various medicaments intended to increase the amount of dopamine present in the brain.

As dopamine does not cross the hematoencephalic barrier, levodopa, a precursor of dopamine converted to dopamine by dopa decarboxylase, was developed in the 1960s. Levodopa remains today the first treatment of choice for Parkinson's disease and initially gives good results. However, after several years, fluctuations in response (on-off effect), a decrease in its effectiveness as the disease progresses (wearing-off effect) and, in particular, dyskinesias (involuntary abnormal movements) are observed in the majority of patients. A psychotic state may also be observed.

Other medicaments, such as dopaminergic agonists, are also recommended, alone or in combination with levodopa, and have as main aim that of reducing at least the undesirable effects of the latter. For some years, selective inhibitors of monoamine oxidase MAO-B, an enzyme which decomposes dopamine in the brain, and inhibitors of catechol-O-methyl transferase (COMT), an enzyme which prevents levodopa from crossing the hematoencephalic barrier, have been developed and prescribed in combination with levodopa. Significant side effects have also been observed with these therapies.

All of the references described herein are incorporated herein by reference in their entirety.

SUMMARY OF THE INVENTION

In order to overcome the above-mentioned disadvantages, it has been found that the combination of one or more CB1 receptor antagonists and of one or more products which activate dopaminergic neurotransmission in the brain exhibits a synergistic effect in the treatment of Parkinson's disease. This is because this combination would make it possible to potentiate the symptomatic effects of a dopaminergic monotherapy (levodopa, dopaminergic agonists and enzyme inhibitors) and would make it possible to reduce the side effects, in particular dyskinesias.

DETAILED DESCRIPTION OF THE INVENTION

In addition to levodopa, a precursor of dopamine, mention may be made, among dopaminergic agonists, of the following products: bromocriptine (Novartis), cabergoline (Pharmacia Corp.), adrogolide (Abbott Laboratories), BAM-1110 (Maruko Seiyaku Co Ltd), Duodopa® (Neopharma), L-dopa, dopadose (Neopharma), CHF1512 (Chiesi), PNU-95666 (Pharmacia & Upjohn), ropinirole (GlaxoSmithKline Beecham), pramipexole (Boehringer, Ingelheim), rotigotine (Discovery Therapeutics, Lohmann Therapy System), spheramine (Titan Pharmaceuticals), TV1203 (Teva Pharmaceutical) or uridine (Polifarma).

Mention may be made, among $MAO_B$ inhibitors, of: rasagiline (Teva Pharmaceutical Ind.), selegiline (RPScherer Corp./Elan) or SL340026 (Sanofi-Synthelabo).

Mention may be made, among COMT inhibitors, of: tolcapone (Roche) and entacapone (Orion Pharma).

A subject-matter of the invention is therefore the combination of one or more products which activate dopaminergic neurotransmission in the brain and of one or more CB1 antagonist azetidine derivatives of formula (I).

Use may in particular be made, among CB1 antagonists, of the azetidine derivatives disclosed in WO 00/15609 of formula:

in which
R represents a chain

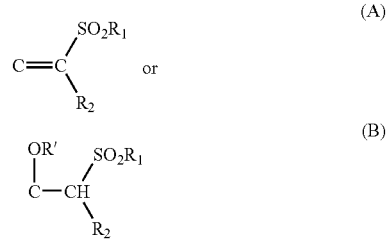

$R_1$ represents a methyl or ethyl radical,
$R_2$ represents either an aromatic radical chosen from phenyl, naphthyl or indenyl, these aromatic radicals being unsubstituted or substituted by one or more halogen, alkyl, alkoxy, —CO-alk, hydroxyl, —COOR$_5$, formyl, trifluoromethyl, trifluoromethylsulfanyl, trifluoromethoxy, nitro, —NR$_6$R$_7$, —CO—NH—NR$_6$R$_7$, —N(alk)COOR$_8$, cyano, —CONHR$_9$, —CO—NR$_{16}$R$_{17}$, alkylsulfanyl, hydroxyalkyl, —O-alk-NR$_{12}$R$_{13}$ or alkylthioalkyl, or a heteroaromatic radical chosen from the benzofuryl, benzothiazolyl, benzothienyl, benzoxazolyl, chromanyl, 2,3-dihydrobenzofuryl, 2,3-dihydrobenzothienyl, indolinyl, indolyl, isochromanyl, isoquinolyl, pyridyl, quinolyl, 1,2,3,4-tetrahydroisoquinolyl, 1,2,3,4-tetrahydroquinolyl, thiazolyl and thienyl rings, it being possible for these heteroaromatic radicals to be unsubstituted or substituted by a halogen, alkyl, alkoxy, —COOR$_5$, trifluoromethyl, trifluoromethylsulfanyl, trifluoromethoxy, nitro, —NR$_6$R$_7$, —CO—NH—NR$_6$R$_7$, cyano, —CONHR$_9$, alkylsulfanyl, hydroxyalkyl or alkylthioalkyl, R$_3$ and R$_4$, which are identical or different, represent either an aromatic radical chosen from phenyl, naphthyl or indenyl, these aromatic radicals being unsubstituted or substituted by one or more halogen, alkyl, alkoxy, formyl, hydroxyl, trifluoromethyl, trifluoromethoxy, —CO-alk, cyano, —COOR$_5$, —CONR$_{10}$R$_{11}$, —CO—NH—NR$_6$R$_7$, alkylsulfanyl, hydroxyalkyl, -alk-NR$_6$R$_7$ or alkylthioalkyl, or a heteroaromatic radical chosen from the benzofuryl, benzothiazolyl, benzothienyl, benzoxazolyl, chromanyl, 2,3-dihydrobenzofuryl, 2,3-dihydrobenzothienyl, furyl, isochromanyl, isoquinolyl, pyrrolyl, quinolyl, 1,2,3,4-tetrahydroisoquinolyl, thiazolyl and thienyl rings, it being possible for these heteroaromatic radicals to be unsubstituted or substituted by a halogen, alkyl, alkoxy, hydroxyl, trifluoromethyl, trifluoromethoxy, cyano, —COOR$_5$, —CO—NH—NR$_6$R$_7$, —CONR$_{10}$R$_{11}$, -alk-NR$_6$R$_7$, alkylsulfanyl, hydroxyalkyl or alkylthioalkyl, R$_5$ is an alkyl radical or a phenyl radical optionally substituted by one or more halogen atoms, R$_6$ and R$_7$, which are identical or different, represent a hydrogen atom or an alkyl, —COOalk, cycloalkyl, alkylcycloalkyl, -alk-O-alk or hydroxyalkyl radical or else R$_6$ and R$_7$ form, together with the nitrogen atom to which they are attached, a saturated or unsaturated and mono- or bicyclic heterocycle having 3 to 10 ring members optionally comprising another heteroatom chosen from oxygen, sulfur and nitrogen and optionally being substituted by one or more alkyl, —COalk, —COOalk, —CO—NHalk, —CS—NHalk, —CO-alk-NR$_{14}$R$_{15}$, oxo, hydroxyalkyl, -alk-O-alk or —CO—NH$_2$ radicals, R$_8$ represents an alkyl radical, R$_9$ represents a hydrogen atom or a radical of the type alkyl or alkyl substituted by dialkylamino, phenyl, cycloalkyl (optionally substituted by —COOalk) or a saturated or unsaturated and mono- or bicyclic heterocycle having 3 to 10 ring members optionally comprising one or more heteroatoms chosen from oxygen, sulfur and nitrogen and optionally being substituted by one or more alkyl radicals, R$_{10}$ and R$_{11}$, which are identical or different, represent a hydrogen atom or an alkyl radical or else R$_{10}$ and R$_{11}$ form, together with the nitrogen atom to which they are attached, a saturated mono- or bicyclic heterocycle having 3 to 10 ring members optionally comprising another heteroatom chosen from oxygen, sulfur and nitrogen and optionally being substituted by an alkyl radical, R$_{12}$ and R$_{13}$, which are identical or different, represent a hydrogen atom or an alkyl or cycloalkyl radical or else R$_{12}$ and R$_{13}$ form, together with the nitrogen atom to which they are attached, a saturated mono- or bicyclic heterocycle having 3 to 10 ring members optionally comprising another heteroatom chosen from oxygen, sulfur and nitrogen and optionally being substituted by an alkyl, —COalk, —COOalk, —CO—NHalk, —CS—NHalk or —CO-alk-NR$_{14}$R$_{15}$ radical or a saturated mono- or bicyclic heterocycle having 3 to 10 ring members and comprising a heteroatom chosen from oxygen, sulfur and nitrogen, R$_{14}$ and R$_{15}$, which are identical or different, represent a hydrogen atom or an alkyl or —COOalk radical, R$_{16}$ and R$_{17}$ form, together with the nitrogen atom to which they are attached, a saturated mono- or bicyclic heterocycle having 3 to 10 ring members optionally comprising another heteroatom chosen from oxygen, sulfur and nitrogen, R' represents a hydrogen atom or a —CO-alk radical, alk represents an alkyl or alkylene radical, it being understood that the alkyl and alkylene radicals and portions and the alkoxy radicals and portions have straight or branched chains and comprise 1 to 6 carbon atoms, their optical isomers (enantiomers and diastereoisomers) and their pharmaceutically acceptable salts.

Mention may be made, among the preferred azetidine derivatives which are a subject-matter of the present invention, of the following derivatives:

1-benzhydryl-3-[(methylsulfonyl)(phenyl)methylene]azetidine, 1-benzhydryl-3-[(3-methylphenyl)(methylsulfonyl)methylene]azetidine, 1-benzhydryl-3-[(3-chlorophenyl)(methylsulfonyl)methylene]azetidine, 1-benzhydryl-3-[(3,5-dichlorophenyl)(methylsulfonyl)methylene]azetidine, 1-benzhydryl-3-[(2,5-dichlorophenyl)(methylsulfonyl)methylene]azetidine, 1-benzhydryl-3-[(2,3-dichlorophenyl)(methylsulfonyl)methylene]azetidine, 1-benzhydryl-3-[(3-fluorophenyl)(methylsulfonyl)methylene]azetidine, 1-benzhydryl-3-[(3,5-difluorophenyl)(methylsulfonyl)methylene]azetidine, 1-benzhydryl-3-[(3-bromophenyl)(methylsulfonyl)methylene]azetidine, 1-benzhydryl-3-[(3-iodophenyl)(methylsulfonyl)methylene]azetidine, 1-benzhydryl-3-[(methylsulfonyl)(3-trifluoromethoxyphenyl)methylene]azetidine, 1-benzhydryl-3-[(methylsulfonyl)(3-trifluoromethylphenyl)methylene]azetidine, 1-benzhydryl-3-{[3,5-bis(trifluoromethyl)phenyl]-(methylsulfonyl)methylene}azetidine, 1-benzhydryl-3-[(3,5-dibromophenyl)(methylsulfonyl)methylene]azetidine, 1-benzhydryl-3-[(3-methoxycarbonylphenyl)(methylsulfonyl)methylene]azetidine, 1-benzhydryl-3-[(3-cyanophenyl)(methylsulfonyl)methylene]azetidine, 1-benzhydryl-3-[(3-carbamoylphenyl)(methylsulfonyl)methylene]azetidine, 1-benzhydryl-3-[(methylsulfonyl)(naphth-1-yl)(methylsulfonyl)methylene]azetidine, 1-[bis(4-chlorophenyl)methyl]-3-[(3,5-difluorophenyl)(methylsulfonyl)methylene]azetidine, 1-[bis(4-methoxyphenyl)methyl]-3-[(3,5-difluorophenyl)(methylsulfonyl)methylene]azetidine, 1-[bis(4-methylphenyl)methyl]-3-[(3,5-difluorophenyl)(methylsulfonyl)methylene]azetidine, (RS)-3-[(3,5-difluorophenyl)(methylsulfonyl)methylene]-1-[(4-methoxyphenyl)(phenyl)methyl)]azetidine,
(R)-3-[(3,5-difluorophenyl)(methylsulfonyl)methylene]-1-[(4-methoxyphenyl)(phenyl)methyl]azetidine,
(S)-3-[(3,5-difluorophenyl)(methylsulfonyl)methylene]-1-[(4-methoxyphenyl)(phenyl)methyl]azetidine,
1-[bis(4-trifluoromethoxyphenyl)methyl]-3-[(3,5-difluorophenyl)(methylsulfonyl)methylene]azetidine,
1-[bis(4-trifluoromethylphenyl)methyl]-3-[(3,5-difluorophenyl)(methylsulfonyl)methylene]azetidine,
1-[bis(4-chlorophenyl)methyl]-3-{[3,5-bis(trifluoromethyl)phenyl](methylsulfonyl)methylene}azetidine,
(RS)-1-[(4-chlorophenyl)(2,4-dichlorophenyl)methyl]-3-[(3,5-difluorophenyl)(methylsulfonyl)methylene]azetidine,
(R)-1-[(4-chlorophenyl)(2,4-dichlorophenyl)methyl]-3-[(3,5-difluorophenyl)(methylsulfonyl)methylene]azetidine,
(S)-1-[(4-chlorophenyl)(2,4-dichlorophenyl)methyl]-3-[(3,5-difluorophenyl)(methylsulfonyl)methylene]azetidine,
(RS)-1-{(4-chlorophenyl)[4-(hydroxymethyl)phenyl]methyl}-3-[(3,5-difluorophenyl)(methylsulfonyl)methylene]azetidine,
(R)-1-{(4-chlorophenyl)[4-(hydroxymethyl)phenyl]methyl}-3-[(3,5-difluorophenyl)(methylsulfonyl)methylene]azetidine,
(S)-1-{(4-chlorophenyl)[4-(hydroxymethyl)phenyl]methyl}-3-[(3,5-difluorophenyl)(methylsulfonyl)methylene]azetidine,
(RS)-1-{(4-chlorophenyl)[4-(pyrrolidinylmethyl)phenyl]methyl}-3-[(3,5-difluorophenyl)(methylsulfonyl)methylene]azetidine,
(R)-1-{(4-chlorophenyl)[4-(pyrrolidinylmethyl)phenyl]methyl}-3-[(3,5-difluorophenyl)(methylsulfonyl)methylene]azetidine,
(S)-1-{(4-chlorophenyl)[4-(pyrrolidinylmethyl)phenyl]methyl}-3-[(3,5-difluorophenyl)(methylsulfonyl)methylene]azetidine,
1-{(RS)-(4-chlorophenyl)[4-(3,3-dimethylpiperidin-1-ylmethyl)phenyl]methyl}-3-[(3,5-difluorophenyl)(methylsulfonyl)methylene]azetidine,
1-{(R)-(4-chlorophenyl)[4-(3,3-dimethylpiperidin-1-ylmethyl)phenyl]methyl}-3-[(3,5-difluorophenyl)(methylsulfonyl)methylene]azetidine,
1-{(S)-(4-chlorophenyl)[4-(3,3-dimethylpiperidin-1-ylmethyl)phenyl]methyl}-3-[(3,5-difluorophenyl)(methylsulfonyl)methylene]azetidine,
1-{(RS)-(4-chlorophenyl)[4-(thiomorpholin-4-ylmethyl)phenyl]methyl}-3-[(3,5-difluorophenyl)(methylsulfonyl)methylene]azetidine,
1-{(R)-(4-chlorophenyl)[4-(thiomorpholin-4-ylmethyl)phenyl]methyl}-3-[(3,5-difluorophenyl)(methylsulfonyl)methylene]azetidine,
1-{(S)-(4-chlorophenyl)[4-(thiomorpholin-4-ylmethyl)phenyl]methyl}-3-[(3,5-difluorophenyl)(methylsulfonyl)methylene]azetidine,
1-{(RS)-(4-chlorophenyl)[4-(N-ethyl-N-cyclohexylaminomethyl)phenyl]methyl}-3-[(3,5-difluorophenyl)(methylsulfonyl)methylene]azetidine,
1-{(R)-(4-chlorophenyl)[4-(N-ethyl-N-cyclohexylaminomethyl)phenyl]methyl}-3-[(3,5-difluorophenyl)(methylsulfonyl)methylene]azetidine,
1-{(S)-(4-chlorophenyl)[4-(N-ethyl-N-cyclohexylaminomethyl)phenyl]methyl}-3-[(3,5-difluorophenyl)(methylsulfonyl)methylene]azetidine,
1-{{(RS)-(4-chlorophenyl){4-[(4-ethoxycarbonyl-piperazinyl)methyl]phenyl}methyl}}-3-[(3,5-difluorophenyl)(methylsulfonyl)methylene]azetidine,
1-{{(R)-(4-chlorophenyl){4-[(4-ethoxycarbonyl-piperazinyl)methyl]phenyl}methyl}}-3-[(3,5-difluorophenyl)(methylsulfonyl)methylene]azetidine,
1-{{(S)-(4-chlorophenyl){4-[(4-ethoxycarbonyl-piperazinyl)methyl]phenyl}methyl}}-3-[(3,5-difluorophenyl)(methylsulfonyl)methylene]azetidine,
1-{(RS)-(4-chlorophenyl)[4-(N-cyclopropyl-N-propylaminomethyl)phenyl]methyl}-3-[(3,5-difluorophenyl)(methylsulfonyl)methylene]azetidine,
1-{(R)-(4-chlorophenyl)[4-(N-cyclopropyl-N-propylaminomethyl)phenyl]methyl}-3-[(3,5-difluorophenyl)(methylsulfonyl)methylene]azetidine,
1-{(S)-(4-chlorophenyl)[4-(N-cyclopropyl-N-propylaminomethyl)phenyl]methyl}-3-[(3,5-difluorophenyl)(methylsulfonyl)methylene]azetidine,
1-{(RS)-(4-chlorophenyl)[4-(diisopropylamino-methyl)phenyl]methyl}-3-[(3,5-difluorophenyl)-(methylsulfonyl)methylene]azetidine,
1-{(R)-(4-chlorophenyl)[4-(diisopropylaminomethyl)-phenyl]methyl}-3-[(3,5-difluorophenyl)(methylsulfonyl)methylene]azetidine,
1-{(S)-(4-chlorophenyl)[4-(diisopropylaminomethyl)phenyl]methyl}-3-[(3,5-difluorophenyl)(methylsulfonyl)methylene]azetidine,
1-{{(RS)-(4-chlorophenyl){4-[bis(2-methoxyethyl)aminomethyl]phenyl}methyl}}-3-[(3,5-difluorophenyl)(methylsulfonyl)methylene]azetidine,
1-{{(R)-(4-chlorophenyl){4-[bis(2-methoxyethyl)aminomethyl]phenyl}methyl}}-3-[(3,5-difluorophenyl)(methylsulfonyl)methylene]azetidine,
1-{{(S)-(4-chlorophenyl){4-[bis(2-methoxyethyl)aminomethyl]phenyl}methyl}}-3-[(3,5-difluorophenyl)(methylsulfonyl)methylene]azetidine,
1-{(RS)-(4-chlorophenyl)[4-[di(n-propyl)aminomethyl)phenyl]methyl}-3-[(3,5-difluorophenyl)(methylsulfonyl)methylene]azetidine,
1-{(R)-(4-chlorophenyl)[4-(di(n-propyl)aminomethyl)phenyl]methyl}-3-[(3,5-difluorophenyl)(methylsulfonyl)methylene]azetidine,
1-{(S)-(4-chlorophenyl)[4-(di(n-propyl)aminomethyl)phenyl]methyl}-3-[(3,5-difluorophenyl)(methylsulfonyl)methylene]azetidine,
1-{(RS)-(4-chlorophenyl)[4-(piperidin-1-ylmethyl)phenyl]methyl}-3-[(3,5-difluorophenyl)(methylsulfonyl)methylene]azetidine,
1-{(R)-(4-chlorophenyl)[4-(piperidin-1-ylmethyl)phenyl]methyl}-3-[(3,5-difluorophenyl)(methylsulfonyl)methylene]azetidine,
1-{(S)-(4-chlorophenyl)[4-(piperidin-1-ylmethyl)phenyl]methyl}-3-[(3,5-difluorophenyl)(methylsulfonyl)methylene]azetidine,
1-{(RS)-(4-chlorophenyl)[4-(4-methylpiperazin-1-ylmethyl)phenyl]methyl}-3-[(3,5-difluorophenyl)(methylsulfonyl)methylene]azetidine,
1-{(R)-(4-chlorophenyl)[4-(4-methylpiperazin-1-ylmethyl)phenyl]methyl}-3-[(3,5-difluorophenyl)(methylsulfonyl)methylene]azetidine,
1-{(S)-(4-chlorophenyl)[4-(4-methylpiperazin-1-ylmethyl)phenyl]methyl}-3-[(3,5-difluorophenyl)(methylsulfonyl)methylene]azetidine,
1-{(RS)-(4-chlorophenyl)[4-(morpholin-4-ylmethyl)phenyl]methyl}-3-[(3,5-difluorophenyl)(methylsulfonyl)methylene]azetidine,
1-{(R)-(4-chlorophenyl)[4-(morpholin-4-ylmethyl)phenyl]methyl}-3-[(3,5-difluorophenyl)(methylsulfonyl)methylene]azetidine, 1-{(S)-(4-chlorophenyl)[4-(morpholin-4-ylmethyl)phenyl]methyl}-3-[(3,5-difluorophenyl)(methylsulfonyl)methylene]azetidine,
1-{(RS)-(4-chlorophenyl)[4-(diethylaminomethyl)phenyl]methyl}-3-[(3,5-difluorophenyl)(methylsulfonyl)methylene]azetidine,
1-{(R)-(4-chlorophenyl)[4-(diethylaminomethyl)phenyl]methyl}-3-[(3,5-difluorophenyl)(methylsulfonyl)methylene]azetidine,
1-{(S)-(4-chlorophenyl)[4-(diethylaminomethyl)phenyl]methyl}-3-[(3,5-difluorophenyl)(methylsulfonyl)methylene]azetidine,
1-{(RS)-(4-chlorophenyl)[4-(piperazin-2-one-4-ylmethyl)phenyl]methyl}-3-[(3,5-difluorophenyl)(methylsulfonyl)methylene]azetidine,
1-{(R)-(4-chlorophenyl)[4-(piperazin-2-one-4-ylmethyl)phenyl]methyl}-3-[(3,5-difluorophenyl)(methylsulfonyl)methylene]azetidine,
1-{(S)-(4-chlorophenyl)[4-(piperazin-2-one-4-ylmethyl)phenyl]methyl}-3-[(3,5-difluorophenyl)(methylsulfonyl)methylene]azetidine,
1-{(RS)-(4-chlorophenyl)[4-(imidazol-1-ylmethyl)phenyl]methyl}-3-[(3,5-difluorophenyl)(methylsulfonyl)methylene]azetidine,
1-{(R)-(4-chlorophenyl)[4-(imidazol-1-ylmethyl)phenyl]methyl}-3-[(3,5-difluorophenyl)(methylsulfonyl)methylene]azetidine,
1-{(S)-(4-chlorophenyl)[4-(imidazol-1-ylmethyl)phenyl]methyl}-3-[(3,5-difluorophenyl)(methylsulfonyl)methylene]azetidine,
(RS)-1-{(4-chlorophenyl)[4-(N,N-dimethylcarbamoyl)phenyl]methyl}-3-[(3,5-difluorophenyl)(methylsulfonyl)methylene]azetidine,
(R)-1-{(4-chlorophenyl)[4-(N,N-dimethylcarbamoyl)phenyl]methyl}-3-[(3,5-difluorophenyl)(methylsulfonyl)methylene]azetidine,
(S)-1-{(4-chlorophenyl)[4-(N,N-dimethylcarbamoyl)phenyl]methyl}-3-[(3,5-difluorophenyl)(methylsulfonyl)methylene]azetidine,
(RS)-1-{(4-chlorophenyl)[4-(N-ethylcarbamoyl)phenyl]methyl)}-3-[(3,5-difluorophenyl)(methylsulfonyl)methylene]azetidine,
(R)-1-{(4-chlorophenyl)[4-(N-ethylcarbamoyl)phenyl]methyl}-3-[(3,5-difluorophenyl)(methylsulfonyl)methylene]azetidine,
(S)-1-{(4-chlorophenyl)[4-(N-ethylcarbamoyl)phenyl]methyl}-3-[(3,5-difluorophenyl)(methylsulfonyl)methylene]azetidine,
(RS)-1-[(4-carbamoylphenyl)(4-chlorophenyl)methyl]-3-[(3,5-difluorophenyl)(methylsulfonyl)methylene]-azetidine,
(R)-1-[(4-carbamoylphenyl)(4-chlorophenyl)methyl]-3-[(3,5-difluorophenyl)(methylsulfonyl)methylene]-azetidine,
(S)-1-[(4-carbamoylphenyl)(4-chlorophenyl)methyl]-3-[(3,5-difluorophenyl)(methylsulfonyl)methylene]-azetidine,
1-[bis(4-chlorophenyl)methyl]-3-[(3,5-dichlorophenyl)(methylsulfonyl)methylene]azetidine,
1-benzhydryl-3-[(3-methylsulfanylphenyl)(methylsulfonyl)methylene]azetidine,
1-benzhydryl-3-[(3-methylsulfanylmethyl)phenyl)]-(methylsulfonyl)methylene]azetidine,
1-[bis(4-chlorophenyl)methyl]-3-[(3-cyanophenyl)(methylsulfonyl)methylene]azetidine,
1-[bis(4-chlorophenyl)methyl]-3-[(3-carbamoylphenyl)(methylsulfonyl)methylene]azetidine,
1-[bis(4-chlorophenyl)methyl]-3-[(3-methoxyphenyl)(methylsulfonyl)methylene]azetidine,
1-[bis(4-chlorophenyl)methyl]-3-[(3-hydroxyphenyl)(methylsulfonyl)methylene]azetidine,
1-[bis(4-chlorophenyl)methyl]-3-[(methylsulfonyl)(3-pyrrolidinylphenyl)methylene]azetidine,
1-[bis(4-chlorophenyl)methyl]-3-[(3-hydroxymethylphenyl)(methylsulfonyl)methylene]azetidine,
1-[bis(4-chlorophenyl)methyl]-3-{(methylsulfonyl)[3-(N-piperidinylcarbamoyl)phenyl]methylene}azetidine,
1-[bis(4-chlorophenyl)methyl]-3-[(methylsulfonyl)(3-trifluoromethylsulfanylphenyl)(methylsulfonyl)methylene]azetidine,
1-[bis(4-fluorophenyl)methyl]-3-[(3,5-difluorophenyl)(methylsulfonyl)methylene]azetidine,
1-[bis(2-fluorophenyl)methyl]-3-[(3,5-difluorophenyl)(methylsulfonyl)methylene]azetidine,
1-[bis(3-fluorophenyl)methyl]-3-[(3,5-difluorophenyl)(methylsulfonyl)methylene]azetidine,
(RS)-1-[(4-chlorophenyl)(thiazol-2-yl)methyl]-3-[(methylsulfonyl)(phenyl)methylene]azetidine,
(R)-1-[(4-chlorophenyl)(thiazol-2-yl)methyl]-3-[(methylsulfonyl)(phenyl)methylene]azetidine,
(S)-1-[(4-chlorophenyl)(thiazol-2-yl)methyl]-3-[(methylsulfonyl)(phenyl)methylene]azetidine,
(RS)-1-[(4-chlorophenyl)(thien-2-yl)methyl]-3-[(3,5-difluorophenyl)(methylsulfonyl)methylene]azetidine,
(R)-1-[(4-chlorophenyl)(thien-2-yl)methyl]-3-[(3,5-difluorophenyl)(methylsulfonyl)methylene]azetidine,
(S)-1-[(4-chlorophenyl)(thien-2-yl)methyl]-3-[(3,5-difluorophenyl)(methylsulfonyl)methylene]azetidine,
1-benzhydryl-3-[(ethylsulfonyl)(phenyl)methylene]-azetidine,
1-[bis(4-chlorophenyl)methyl]-3-{{3-[N-(4-methylpiperazinyl)carbamoyl]phenyl}(methylsulfonyl)methylene}azetidine,
1-[bis(4-chlorophenyl)methyl]-3-{[3-(2,2-dimethylcarbohydrazido)phenyl](methylsulfonyl)methylene}azetidine,
1-[bis(thien-2-yl)methyl]-3-[(3,5-difluorophenyl)(methylsulfonyl)methylene]azetidine,
1-[bis(p-tolyl)methyl]-3-[(methylsulfonyl)(phenyl)methylene]azetidine,
1-[(4-chlorophenyl)(4-hydroxymethylphenyl)methyl]-3-[(3,5-difluorophenyl)(methylsulfonyl)methylene]-azetidine,
1-[bis(4-chlorophenyl)methyl]-3-[(3-methylaminophenyl)(methylsulfonyl)methylene]azetidine,
(RS)-1-[(4-chlorophenyl)(thiazol-2-yl)methyl]-3-[(3,5-difluorophenyl)(methylsulfonyl)methylene]azetidine,
(R)-1-[(4-chlorophenyl)(thiazol-2-yl)methyl]-3-[(3,5-difluorophenyl)(methylsulfonyl)methylene]azetidine,
(S)-1-[(4-chlorophenyl)(thiazol-2-yl)methyl]-3-[(3,5-difluorophenyl)(methylsulfonyl)methylene]azetidine,
1-[bis(4-chlorophenyl)methyl]-3-[(methylsulfonyl)(2-methoxycarbonylthien-5-yl)methylene]azetidine,
(RS)-1-[bis(4-chlorophenyl)methyl]-3-hydroxy-3-[(methylsulfonyl)(2-methoxycarbonylthien-5-yl)methyl]azetidine,
1-[bis(4-chlorophenyl)methyl]-3-[(2-isobutylaminocarbonylthien-5-yl)(methylsulfonyl)methylene]azetidine,
1-[bis(4-chlorophenyl)methyl]-3-[(RS)-(3-methoxycarbonylphenyl)(methylsulfonyl)methyl]azetidin-3-ol,
1-[bis(4-chlorophenyl)methyl]-3-[(RS)-(methylsulfonyl)(pyridin-4-yl)methyl]azetidin-3-ol,
1-[bis(4-chlorophenyl)methyl]-3-[(RS)-(methylsulfonyl)(pyridin-3-yl)methyl]azetidin-3-ol,
3-({1-[bis(4-chlorophenyl)methyl]azetidin-3-ylidene}(methanesulfonyl)methyl)-N-(3-(morpholin-4-yl)propyl)benzamide, 3-({1-[bis(4-chlorophenyl)methyl]azetidin-3-ylidene}(methanesulfonyl)methyl)-N-(3-dimethylaminopropyl)benzamide,
3-({1-[bis(4-chlorophenyl)methyl]azetidin-3-ylidene}(methanesulfonyl)methyl)-N-(2-(pyrrolidin-1-yl)ethyl)benzamide,
3-({1-[bis(4-chlorophenyl)methyl]azetidin-3-ylidene}(methanesulfonyl)methyl)-N-(2-dimethylamino-1-methylethyl)benzamide,
3-({1-[bis(4-chlorophenyl)methyl]azetidin-3-ylidene}(methanesulfonyl)methyl)-N-(piperidin-1-yl)benzamide,
3-({1-[bis(4-chlorophenyl)methyl]azetidin-3-ylidene}(methanesulfonyl)methyl)-N-isobutylbenzamide,
3-({1-[bis(4-chlorophenyl)methyl]azetidin-3-ylidene}(methanesulfonyl)methyl)-N-(3-(imidazol-1-yl)propyl)benzamide,
3-({1-[bis(4-chlorophenyl)methyl]azetidin-3-ylidene}(methanesulfonyl)methyl)-N-(2-dimethylaminoethyl)benzamide,
N'-methylhydrazide of 3-({1-[bis(4-chlorophenyl)methyl]azetidin-3-ylidene}(methanesulfonyl)methyl)benzoic acid,
3-({1-[bis(4-chlorophenyl)methyl]azetidin-3-ylidene}(methanesulfonyl)methyl)-N-(2-(morpholin-4-yl)ethyl)benzamide,
3-({1-[bis(4-chlorophenyl)methyl]azetidin-3-ylidene}(methanesulfonyl)methyl)-N-(1-ethylpyrrolidin-2-ylmethyl)benzamide,
3-({1-[bis(4-chlorophenyl)methyl]azetidin-3-ylidene}(methanesulfonyl)methyl)-N-(2,2-dimethylpropyl)benzamide,
3-({1-[bis(4-chlorophenyl)methyl]azetidin-3-ylidene}(methanesulfonyl)methyl)-N-(cyclohexylmethyl)benzamide,
3-({1-[bis(4-chlorophenyl)methyl]azetidin-3-ylidene}(methanesulfonyl)methyl)-N-(cyclopropylmethyl)benzamide,
3-({1-[bis(4-chlorophenyl)methyl]azetidin-3-ylidene}(methanesulfonyl)methyl)-N-(2-methylbutyl)benzamide,
3-({1-[bis(4-chlorophenyl)methyl]azetidin-3-ylidene}(methanesulfonyl)methyl)-N-(2-phenylpropyl)benzamide,
3-({1-[bis(4-chlorophenyl)methyl]azetidin-3-ylidene}(methanesulfonyl)methyl)-N-(tetrahydrofuran-2-ylmethyl)benzamide,
3-({1-[bis(4-chlorophenyl)methyl]azetidin-3-ylidene}(methanesulfonyl)methyl)-N-(2,2-diphenylethyl)benzamide,
3-({1-[bis(4-chlorophenyl)methyl]azetidin-3-ylidene}(methanesulfonyl)methyl)-N-(2-ethylbutyl)benzamide,
methyl ester of 4-{([3-({1-[bis(4-chlorophenyl)methyl]azetidin-3-ylidene}(methanesulfonyl)methyl)benzoylamino]methyl}cyclohexanecarboxylic acid,
2-amino-1-{4-[3-({1-[bis(4-chlorophenyl)methyl]azetidin-3-ylidene}(methanesulfonyl)methyl)phenyl]piperazin-1-yl}ethanone,
tert-butyl ester of (2-{4-[3-({1-[bis(4-chlorophenyl)methyl]azetidin-3-ylidene}(methanesulfonyl)methyl)phenyl]piperazin-1-yl}-2-oxoethyl)carbamic acid,
1-{4-[3-({1-[bis(4-chlorophenyl)methyl]azetidin-3-ylidene}(methanesulfonyl)methyl)phenyl]piperazin-1-yl}-2-(methylamino)ethanone,
tert-butyl ester of (2-{4-[3-({1-[bis(4-chlorophenyl)methyl]azetidin-3-ylidene}(methanesulfonyl)methyl)phenyl]piperazin-1-yl}-2-oxoethyl)-N-methylcarbamic acid,
N-methylamide of 4-[3-({1-[bis(4-chlorophenyl)methyl]azetidin-3-ylidene}(methanesulfonyl)methyl)phenyl]piperazine-1-carboxylic acid,
N-methylamide of 4-[3-({1-[bis(4-chlorophenyl)methyl]azetidin-3-ylidene}(methanesulfonyl)methyl)phenyl]-piperazine-1-carboxylic acid,
methyl ester of 4-[3-({1-[bis(4-chlorophenyl)methyl]-azetidin-3-ylidene}(methanesulfonyl)methyl)phenyl]piperazine-1-carboxylic acid,
1-[3-({1-[bis(4-chlorophenyl)methyl]azetidin-3-ylidene}(methanesulfonyl)methyl)phenyl]-4-isobutylpiperazine,
1-[3-({1-[bis(4-chlorophenyl)methyl]azetidin-3-ylidene}(methanesulfonyl)methyl)phenyl]-4-ethylpiperazine,
4-acetyl-1-[3-({1-[bis(4-chlorophenyl)methyl]azetidin-3-ylidene}(methanesulfonyl)methyl)phenyl]piperazine,
1-{4-[3-({1-[bis(4-chlorophenyl)methyl]azetidin-3-ylidene}(methanesulfonyl)methyl)phenyl]piperazin-1-yl}-2-dimethylaminoethanone,
1-[3-({1-[bis(4-chlorophenyl)methyl]azetidin-3-ylidene}(methanesulfonyl)methyl)phenyl]piperazine,
tert-butyl ester of 4-[3-({1-[bis(4-chlorophenyl)methyl]azetidin-3-ylidene}(methanesulfonyl)methyl)phenyl]piperazine-1-carboxylic acid,
1-[bis(4-methoxycarbonylphenyl)methyl]-3-[(3,5-difluorophenyl)(methylsulfonyl)methylene]azetidine,
3-acetoxy-1-[bis(4-methoxycarbonylphenyl)methyl]-3-[(RS)-(3,5-difluorophenyl)(methylsulfonyl)methyl]-azetidine,
(RS)-4-[4-((4-chlorophenyl){3-[(3,5-difluorophenyl)(methanesulfonyl)methylene]azetidin-1-yl}methyl)benzyl]morpholine,
4-(4-{3-[(1-benzhydrylazetidin-3-ylidene)(methanesulfonyl)methyl]phenoxy}butyl)morpholine,
4-(4-{3-[(1-benzhydrylazetidin-3-ylidene)(methanesulfonyl)methyl]phenoxy}propyl)morpholine,
their optical isomers and their pharmaceutically acceptable salts.

And even more particularly preferred are the following azetidine derivatives: 1-[bis(4-chlorophenyl)methyl]-3-[(3,5-difluorophenyl)(methylsulfonyl)methylene]azetidine, and its pharmaceutically acceptable salts.

Mention may be made, as examples of pharmaceutically acceptable salts of the azetidine derivatives, of the following salts: benzenesulfonate, hydrobromide, hydrochloride, citrate, ethanesulfonate, fumarate, gluconate, iodate, isethionate, maleate, methanesulfonate, methylenebis(β-oxynaphthoate), nitrate, oxalate, pamoate, phosphate, salicylate, succinate, sulfate, tartrate, theophyllineacetate and p-toluenesulfonate.

The synergistic effect of the combination of one or more products which activate dopaminergic neurotransmission in the brain and of one or more CB1 antagonists in the treatment of Parkinson's disease was determined in a model of akinesia induced by reserpine in the rat according to the following protocol:

Male Sprague-Dawley rats were treated with reserpine administered subcutaneously at a dose of 3 mg/kg (1 ml/kg) in order to induce akinesia in the animal. 18 hours after this treatment, the locomotor activity of these animals was measured and recorded using an automatic system (Videotrack, France). The locomotion, expressed in centimeters, is estimated by a mean overall distance covered during this period (n=11–38 rats per group). The statistical analysis is carried out by a variance analysis and a post-hoc comparison (if appropriate) using a Mann-Whitney or Dunnett test. A significant effect is recorded for $p<0.05$.

The synergistic effect of the combination is shown in Tables 1 and 2.

Table 1 relates to the ip administration of the CB1 antagonist and Table 2 relates to the po administration of the CB1 antagonist.

The results for the ip administration of the CB1 antagonists (Table 1) are expressed as percentage of increase with respect to the activity of quinpirole and as percentage of decrease with respect to the activity of a very strong dose of levodopa.

The combination of a CB1 receptor antagonist and of a D2 dopaminergic agonist (quinpirole) is produced in the following way:

The CB1 antagonist product (1.5 mg/kg i.p., 2 ml/kg) and quinpirole (62.5 μg/kg i.p., 1 ml/kg) are co-administered 18 hours after the injection of reserpine. The recording of the motor activity begins 5 minutes after the co-administration of the products and lasts 1 hour.

The combination of a CB1 receptor antagonist and of a strong dose of levodopa (dyskinesia model) is produced in the following way:

The CB1 antagonist product (3 mg/kg i.p., 2 ml/kg) and levodopa (120 mg/kg+benserazide, 50 mg/kg i.p., 5 ml/kg) are co-administered. Benserazide is a peripheral dopa-decarboxylase inhibitor which allows levodopa to cross the hematoencephalic barrier before it is converted into dopamine. The recording of the motor activity begins 5 minutes after the co-administration and lasts 2.5 hours.

TABLE 1

| Reserpine-treated rats | Combination with quinpirole (62.5 μg/kg ip) | Combination with levodopa (120 mg/kg ip) |
|---|---|---|
| Example 1 | +125%*** (1.5 mg/kg i.p.) | −42%* (3 mg/kg i.p.) |
| SR141716A 1 mg/kg i.p. | +116%*** | −61%* |

Example 1=1-[bis(4-chlorophenyl)methyl]-3-[(3,5-difluorophenyl)(methylsulfonyl)methylene]azetidine)

SR141716A=N-(piperidin-1-yl)-5-(4-chlorophenyl)-1-(2,4-dichlorophenyl)-4-methyl-1H-pyrazole-3-carboxamide hydrochloride ANOVA+Mann-Whitney: $*p<0.05$, $p<0.01$, $*p<0.001$.

These results according to the invention show that the CB1 receptor antagonists:

significantly potentiate the effects of a D2 dopaminergic agonist (reduction in the symptoms of Parkinson's disease)

and reduce the hyperactivity induced by a very strong dose of levodopa (antidyskinetic activity).

The studies by the oral route are carried out in a hydrophobic formulation solvent Labrafil/Labrasol (40/60%, w/w). These products are administered (in a volume of 1 ml/kg) one hour before the dopaminergic agonist. The recording of the locomotor activity begins 5 min after the intraperitoneal injection of the dopaminergic agonist and lasts 1 hour. The D1 dopaminergic agonist is 0.3 mg/kg C1-APB. The D2 dopaminergic agonist is 0.1 mg/kg quinpirole.

The results for the po administration of the CB1 antagonists are given at three different doses (1, 3 and 10 mg/kg/po) and these results (Table 2) are expressed as percentage of increase with respect to the activity of quinpirole and as percentage of decrease with respect to the activity of a strong dose of C1-APB (SKF 82958).

TABLE 2

|  | Dose mg/kg po | Combination with quinpirole (0.1 mg/kg ip) | Combination with C1-APB (0.3 mg/kg ip) |
|---|---|---|---|
| Examble 1 | 1 | +33% NS | −33% NS |
|  | 3 | +58%** | −67%** |
|  | 10 | +23% NS | −62%** |
| SR141716A | 1 | +57%* NS | −32% NS |
|  | 3 | +121%** | −58%* |
|  | 10 | +87%** | −82%** |

Example 1=1-[bis(4-chlorophenyl)methyl]-3-[(3,5-difluorophenyl)(methylsulfonyl)methylene]azetidine)

SR141716A=N-(piperidin-1-yl)-5-(4-chlorophenyl)-1-(2,4-dichlorophenyl)-4-methyl-1H-pyrazole-3-carboxamide hydrochloride ANOVA+Dunnett: $*p<0.05$, $**p<0.01$ These results according to the invention show that the CB1 receptor antagonists:

significantly potentiate the effects of a D2 dopaminergic agonist (reduction in the symptoms of Parkinson's disease)

and reduce the hyperactivity induced by a strong dose of D1 type (antidyskinetic activity).

The compounds of the combination can be employed orally, parenterally, transdermally or rectally, either simultaneously or separately or spread out over time.

The present invention also relates to the pharmaceutical compositions comprising the combination of one or more products which activate dopaminergic neurotransmission in the brain and of one or more CB1 receptor antagonists as defined above with a pharmaceutically acceptable vehicle.

Use may be made, as solid compositions for oral administration, of tablets, pills, powders (hard gelatin capsules, cachets) or granules. In these compositions, the active principles are mixed with one or more inert diluents, such as starch, cellulose, sucrose, lactose or silica, under an argon stream. These compositions can also comprise substances other than the diluents, for example one or more lubricants, such as magnesium stearate or talc, a colorant, a coating (dragées) or a glaze.

Use may be made, as liquid compositions for oral administration, of pharmaceutically acceptable solutions, suspensions, emulsions, syrups and elixirs comprising inert diluents, such as water, ethanol, glycerol, vegetable oils or liquid paraffin. These compositions can comprise substances other than the diluents, for example wetting, sweetening, thickening, flavoring or stabilizing products.

The sterile compositions for parenteral administration can preferably be solutions in aqueous or nonaqueous form, suspensions or emulsions. Use may be made, as solvent or vehicle, of water, propylene glycol, a polyethylene glycol, vegetable oils, in particular olive oil, injectable organic esters, for example ethyl oleate, or other suitable organic solvents. These compositions can also comprise adjuvants, in particular wetting, isotonizing, emulsifying, dispersing and stabilizing agents. Sterilization can be carried out in several ways, for example by aseptic filtration, by incorporating sterilizing agents in the composition, by irradiation or by heating. They can also be prepared in the form of sterile solid compositions which can be dissolved at the time of use in sterile water or any other injectable sterile medium.

The compositions for rectal administration are suppositories or rectal capsules which comprise, in addition to the active product, excipients such as cocoa butter, semisynthetic glycerides or polyethylene glycols.

The pharmaceutical compositions including the combination as defined above generally comprise 0.1 to 500 mg of the CB1 antagonist. The present invention also relates to the method for the treatment of Parkinson's disease which consists in administering, to the patient, a combination or a pharmaceutical composition including the combination as defined above, either simultaneously or separately or spread out over time.

The doses depend on the desired effect, on the duration of treatment and on the administration route used; they are generally from 0.1 to 500 mg of the CB1 antagonist per day by the oral route for an adult.

Generally, the doctor will determine the appropriate dosage according to the age, weight and any other factor specific to the subject to be treated.

The invention claimed is:

1. A pharmaceutical composition comprising 1-[bis(4-chlorophenyl)methyl]-3-[(3,5-difluorophenyl)(methylsulfonyl)methylene]azetidine or a pharmaceutically acceptable salt thereof and one or more products which activates dopaminergic neurotransmission in the brain.

2. The pharmaceutical composition according to claim 1, wherein the product which activates dopaminergic neurotransmission in the brain is chosen from the following compounds:

bromocriptine, cabergoline, adrogolide, BAM-1110, duodopa, levodapa, dopadose, CHF1512, PNU-95666, ropinirole, pramipexole, rotigotine, spheramine, TV1203, uridine, rasagiline, selegiline, SL340026, tolcapone and entacapone.

3. The pharmaceutical composition according to claim 1, wherein the product which activates dopaminergic neurotransmission in the brain is levodopa.

4. The pharmaceutical composition according to claim 1, wherein the product which activates dopaminergic neurotransmission in the brain is ropinirole.

5. The pharmaceutical composition according to claim 1, wherein the product which activates dopaminergic neurotransmission in the brain is bromocriptine.

6. The pharmaceutical composition according to claim 1, wherein the product which activates dopaminergic neurotransmission in the brain is pramipexole.

7. The pharmaceutical composition according to claim 1, wherein the product which activates dopaminergic neurotransmission in the brain is rasagiline.

8. The pharmaceutical composition according to claim 1, wherein the product which activates dopaminergic neurotransmission in the brain is entacapone.

9. A pharmaceutical composition comprising one or more products which activate dopaminergic neurotransmission in the brain and 1-[bis(4-chlorophenyl)methyl]-3-[(3,5-difluorophenyl)(methylsulfonyl)methylene]-azetidine or a pharmaceutically acceptable salt thereof in combination with a compatible and pharmaceutically acceptable vehicle.

10. The pharmaceutical composition according to claim 9, wherein the product which activates dopaminergic neurotransmission in the brain is chosen from quinpirole, levodopa and C1-APB.

11. The pharmaceutical composition according to claim 9, wherein the product which activates dopaminergic neurotransmission in the brain is chosen from the following compounds:

bromocriptine, cabergoline, talipexole, adrogolide, BAM-1110, duodopa, levodopa, dopadose, CHF1512, PNU-95666, ropinirole, pramipexole, rotigotine, spheramine, TV1203, uridine, rasagiline, selegiline, SL340026, tolcapone and entacapone.

12. The pharmaceutical composition according to claim 9, wherein the product which activates dopaminergic neurotransmission in the brain is levodopa.

13. The pharmaceutical composition according to claim 9, wherein the product which activates dopaminergic neurotransmission in the brain is ropinirole.

14. The pharmaceutical composition according to claim 9, wherein the product which activates dopaminergic neurotransmission in the brain is bromocriptine.

15. The pharmaceutical composition according to claim 9, wherein the product which activates dopaminergic neurotransmission in the brain is pramipexole.

16. The pharmaceutical composition according to claim 9, wherein the product which activates dopaminergic neurotransmission in the brain is rasagiline.

17. The pharmaceutical composition according to claim 9, wherein the product which activates dopaminergic neurotransmission in the brain is entacapone.

18. The pharmaceutical composition according to claim 9, wherein 1-[bis(4-chlorophenyl)methyl]-3-[(3,5difluorophenyl)methylsulfonyl)methylene]-azetidine is present in an amount of from about 0.1 mg to about 500 mg.

19. The pharmaceutical composition according to claim 1, wherein the product which activates dopaminergic neurotransmission in the brain is quinpirole.

20. The pharmaceutical composition according to claim 1, wherein the product which activates dopaminergic neurotransmission in the brain is C1-APB.

21. The pharmaceutical composition according to claim 9, wherein the product which activates dopaminergic neurotransmission in the brain is quinpirole.

22. The pharmaceutical composition according to claim 9, wherein the product which activates dopaminergic neurotransmission in the brain is C1-APB.

* * * * *